United States Patent [19]
Towle

[11] 4,012,333
[45] Mar. 15, 1977

[54] METHOD OF MAKING GELS BASED ON BIOLOGICALLY PRODUCED POLYSACCHARIDES

[75] Inventor: Gordon A. Towle, Landenberg, Pa.

[73] Assignee: Hercules Incorporated, Wilmington, Del.

[22] Filed: May 23, 1975

[21] Appl. No.: 580,262

[52] U.S. Cl. .................................. 252/316; 424/35; 424/76; 424/361; 426/573; 426/660
[51] Int. Cl.² .......................................... B01J 13/00
[58] Field of Search ..................... 252/316; 426/573

[56] References Cited

UNITED STATES PATENTS

| 2,253,297 | 8/1941 | Houghton et al. ............. 252/316 X |
| 3,684,733 | 8/1972 | Bannister et al. ................. 252/316 |
| 3,822,250 | 7/1974 | Kimura et al. ................. 260/209 R |

*Primary Examiner*—Richard D. Lovering
*Attorney, Agent, or Firm*—William S. Alexander

[57] ABSTRACT

Gels are prepared from a biologically produced beta-1,3-glucan-type polysaccharide by exposing a basic solution of the polysaccharide to an atmosphere of a gaseous acid anhydride.

3 Claims, No Drawings

METHOD OF MAKING GELS BASED ON BIOLOGICALLY PRODUCED POLYSACCHARIDES

This invention relates to the preparation of gels of certain polysaccharide materials. In particular, it relates to the preparation of gels suitable for a variety of uses from a biologically produced beta-1,3-glucan-type polysaccharide.

In U.S. Pat. No. 3,822,250, there is disclosed a method of preparing a beta-1,3-glucan-type polysaccharide material by cultivation of certain microorganisms. The microorganisms of interest in this connection are:

a. Agrobacterium radiobacter - ATCC-6466: This strain is available from American Type Culture Collection under the accession number of ATCC-6466;

b. Agrobacterium radiobacter - Strain U-19. This strain is a mutant derived from the parent strain ATCC-6466 by irradiation of ultraviolet rays in a conventional manner and has a unique property that it produces substantially no other polysaccharide. A subculture of this strain has been deposited with Institute for Fermentation, Osaka, Japan, under the accession number of "IFO-13126" and with ATCC under accession number ATCC-21679.

c. Alcaligenes faecalis var. myogenes, Strain NTK-u: This strain is obtained by treating Alcaligenes faecalis var. myogenes, Strain K, with N-methyl-N'-nitro-N-nitrosoguanidine. This strain is available from ATCC under accession number ATCC-21680. Inasmuch as these microorganisms are known entities, further description of them is not deemed necessary here. For a more detailed description, reference can be had to the aforesaid U.S. Pat. No. 3,822,250.

The polysaccharide prepared by cultivation of the specified microorganisms is, as stated above, of the beta-1,3glucan type. Hereinafter, reference to beta-1,3-glucan or to the polysaccharide can be taken to mean such a compound prepared by the action of these microogranisms.

The polysaccharide is substantially insoluble in neutral water at temperatures below about 50° C. although it is swellable. In water at acid pH levels, it forms gels and at pH levels above about 10.5 it is soluble.

A highly interesting property of this polysaccharide is its capacity to form gels possessing excellent water-holding and flavor-binding abilities. The polysaccharide is also non-toxic and pharmacologically and nutritionally inert. Gels prepared therefrom can be taken into the human body safely, affording such gels a variety of applications in the food industry.

The above-referenced U.S. Pat. No. 3,822,250 discusses at great length the formation of gels from the polysaccharides contemplated by this invention and the utilization of such gels in foodstuffs. The technique taught in that reference for gelling the polysaccharide is by heating. The reference teaches that if the polysaccharide is heated to a temperature between about 50° and 200° C., a gel is formed very readily which has excellent gel strength and freeze-thaw stability, is thermally irreversible and retains such favorable properties over a wide pH range from about 1 to 11.5.

British patent No. 1,379,406 teaches the preparation of gels from beta-1,3-glucan by a procedure which involves dissolving the polysaccharide in basic aqueous medium and then removing the base by diffusion, e.g., dialyzing or by neutralization with an acid. Gels can be prepared by this technique in the form of films, thin-walled tubes, filaments or globules. In the gelling process, the basic polysaccharide solution is brought into contact with the acid, whereupon neutralization and gelling take place substantially immediately.

Both of the techniques taught by the prior art are subject to certain objections. There are many instances when heating to effect gelling is an impractical nuisance which it is desirable to avoid if possible. The acid gelling technique is subject to the objection that, except for very thin configurations, it is not useful for forming continuous bodies of gel of any significant size.

It is an object of this invention to provide a technique for gelling the beta-1,3-glucan polysaccharide which overcomes some of the objections just cited. It is a further object to prepare gels having the same favorable combination of properties as those taught by the prior art as well as other properties which are improvements over those possessed by prior art gels.

In accordance with this invention it has now been found that a gel is formed when a solution of a beta-1,3-glucan polysaccharide in basic medium having a pH greater than about 10.5 is subjected to an atmosphere of a gaseous acid anhydride. Stated specifically, the invention is a method of preparing a gel of a beta-1,3-glucan polysaccharide which comprises preparing a solution of said beta-1,3-glucan in an aqueous medium having a pH of at least about 10.5 and subjecting said solution under quiescent conditions to an atmosphere of a gaseous acid anhydride under conditions of time and gas pressure sufficient to cause said anhydride to diffuse through said solution and effect gelling.

The most common gaseous acid anhydrides are carbon dioxide, the oxides of nitrogen such as $NO_2$ or $N_2O_4$ and the like and the oxides of sulfur such as $SO_2$ and $SO_3$. Since the beta-1,3-glucans which are gelled by the process of the invention are extensively employed in foodstuffs, the preferred gas is carbon dioxide. Use of the other gases is limited to applications where the possible presence of the acids of nitrogen and sulfur is not objectionable.

The beta-1,3-glucan must be subjected to the atmosphere of gaseous acid anhydride under quiescent conditions, i.e., there must be no agitation of the polysaccharide while it is exposed to the gas. The gas must be caused or permitted to get into the solution via diffusion rather than by mixing it in. If the solution is not quiescent during the incorporation of the gas, gelling will take place, but the resultant product will not exhibit a firm, continuous gel structure and will have substantially no measurable gel strength. Rather, it will form a plurality of discrete unconnected gel particles, having the consistency of, e.g., apple sauce, rather than the desired firm gel structure.

The pressure employed in the treatment with gaseous acid anhydride can be varied depending upon the concentration of the beta-1,3-glucan in the solution to be gelled and upon the configuration sought in the finished gel. Lower concentrations of the beta1,3-glucan in solution can be gelled in less time and with a lower pressure of the gas than can higher concentrations. Likewise, a thin body of the solution can be gelled more quickly and at a lower pressure than can a thicker body. In fact, a very thin film of the beta-1,3-glucan can gel simply from the effect of $CO_2$ found in the atmosphere if it is exposed to the atmosphere for any significant time. Also, the less basic the solution, the easier it forms a gel, thus lowering the time and pressure requirements to effect gelling.

The efficacy of the gaseous acid anhydride is affected by the pressure of the gas, by the temperature of the gas and the solution, by the concentration of the polysaccharide and by the basicity of the solution. Generally, it is preferred, for the sake of convenience, to operate at the lowest temperature and pressure reasonably possible, i.e., at atmospheric pressure and room temperature. It is necessary to operate at a temperature level at which the solution does not boil, since the turbulence associated with boiling would not permit a continuous gel to form. Generally, the gas pressure on the system will be no greater than about 100 p.s.i.g.

Due to the ease with which the acid anhydride gas can diffuse into thin layers of the polysaccharide solution, the method of the invention is particularly adapted to the preparation of thin films. Such thin films can find use as packaging films, edible coatings and oxygen barrier films.

The solutions to be gelled can contain about 0.1 to 10% of the beta-1,3-glucan in solution. Preferably, they will contain 0.2 to 5% beta-1,3-glucan. Within these ranges sufficient polysaccharide is present to form a gel of whatever gel strength is required without forming a solution which is too viscous to permit diffusion of the gaseous acid anhydride to effect gelling. Gel strength, as with most gel processes, increases as the concentration of the polysaccharide is increased.

As stated, the invention proceeds from a solution of the beta-1,3-glucan in an alkaline medium. The beta-1,3-glucan is relatively insoluble in cold aqueous systems of less than about 10 pH. Thus, in order to form a gel, the pH is raised to about 10.5 or higher, at which point solution occurs quickly and substantially completely. The raising of the pH can be accomplished by any reagent capable of creating the appropriate degree of alkalinity such as, e.g., ammonium hydroxide, trisodium phosphate, sodium carbonate, sodium hydroxide, potassium hydroxide, lithium hydroxide, tripotassium phosphate, potassium carbonate or calcium hydroxide. For food applications, sodium or potassium phosphate are preferred materials for creating the required alkaline environment.

The invention is exemplified in the following examples. Parts and percentages are by weight unless otherwise specified. As stated hereinabove, reference to "polysaccharide" in these examples means the beta-1,3-glucan type polysaccharide produced by cultivation of the microorganisms specified at the beginning of these specifications.

EXAMPLE 1

A 5% solution of polysaccharide in 0.2% NaOH was cast on a Teflon substrate to form a film of 50 mil wet thickness. The film was then exposed at room temperature to $CO_2$ at a pressure of one atmosphere for about 15 minutes. At the end of this time, the film had gelled and was no longer fluid. Further drying in air at ambient temperature gave a hard film which, when stripped from the substrate, was 2 mils in thickness. It was of sparkling clarity and had good flexibility at relative humidities as low as about 30%.

EXAMPLE 2

The procedure of Example 1 was repeated with a solution of polysaccharide containing 20% glycerol, based on the polymer, as a plasticizer. The resulting film retained flexibility at relative humidities as low as 10-15%.

EXAMPLE 3

The procedure of Example 2 was repeated except that the plasticizer was propylene glycol in the amount of 10% based on the polymer. The resulting film retained good flexiblity at low relative humidities.

EXAMPLE 4

The procedure of Example 2 was repeated, except that the plasticizer was sorbitol at 5% concentration, based on the polymer. The resulting film retained good flexibility at low relative humidities.

EXAMPLE 5

A 5% solution of polysaccharide in 0.2% NaOH was prepared and had a pH of about 12. The solution was poured to a depth of several centimeters into a cylindrical container and then exposed to an atmosphere of $CO_2$ for several hours. The resulting gel was firm. In contrast to gels made in the conventional manner by heating neutral suspensions of polysaccharide, the gel of this example showed no syneresis and was of improved clarity. The pH, measured at the top of the gel was 6.9 and at the bottom was 7.4, indicating substantially complete neutralization of the NaOH by $CO_2$.

EXAMPLE 6

A 1% solution of polysaccharide in 0.1% NaOH and a similar solution made up in 0.05% NaOH were poured to a depth of several centimeters into cylindrical containers. The clear solutions were then exposed to $CO_2$ at a pressure of one atmosphere and the rates of gel formation were observed by following the development of the tubid gel layer through the solution. Complete gelation of the solution in 0.1% NaOH required about 50% more time than gelation of the solution in 0.05% NaOH.

EXAMPLE 7

A gelatin-type dessert formulation containing FD+C 2 red dye, raspberry flavor and sugar was placed in a can and sealed in such a manner that the contents were at a pressure of about 60 p.s.i.g. of $CO_2$ pressure. When the can was opened several hours later, the contents were removed as a molded gel of pleasing appearance and aroma, having excellent texture and mouth feel.

EXAMPLE 8

An air freshener formulation containing a green dye and pine oil as an odorant was made up in a 3% solution of polysaccharide in 0.2% NaOH. The formulation was poured into a rectangular plastic container and gelled by exposure to $CO_2$ at one atmosphere pressure. The container was then fitted with a perforated plastic plate to protect the surface of the gel, and finally with an impervious snap-on lid. The impervious lid was removed from the container, whenever it was needed to serve as an air freshener, effectively masking cooking and tobacco odors. Over many hours of service, the gel gradually shrunk in volume and when exhausted had assumed the state of a dark, horny, innocuous mass which could easily be disposed of.

EXAMPLE 9–12

The procedure of Examples 1–4 was followed, substituting $SO_2$ in place of $CO_2$. The resulting films had substantially the same properties as those described earlier.

EXAMPLE 13

A test panel of cold rolled steel was used as a substrate on which a 5% solution of polysaccharide in 0.2% NaOH was cast to a wet thickness of 50 mils. The solution was gelled by exposure to $CO_2$ and the panel was allowed to dry in air. The resulting protective coating was tough and adherent. On spraying with water for several minutes, the film swelled and softened, and could easily be removed with a stiff brush.

EXAMPLE 14

Pharmaceutical tablets were coated with polysaccharide in a regulation pan coater, in which the agitated mass of pellets was sprayed with a 5% solution of the polymer in dilute NaOH. Simultaneously with the spraying, the tablets were subjected to a stream of heated $CO_2$-enriched air to gel the polymer. The stream of heated air was continued for some time after the spraying to dry the polymer completely. The tablets had a hard, shiny polymer coating which served as an effective barrier against moisture and air.

A particular advantage of this invention is that clear strong gels, exhibiting little or no syneresis, can be formed in systems containing large amounts of water-soluble hydroxylated organic compounds such as glycols, polyglycols, sorbitol, mannitol or mono- or di-saccharides. Ordinarily, if 0.5 g. of polysaccharide is suspended in a 65% aqueous sucrose solution and then heated to about 80°, in the manner commonly employed for making thermal gels, no gel results. Even with higher amounts of polysaccharide, if the amount of hydroxylated organic compound is in excess of about 25%, either no gel will be formed or the gel will be weak and exhibit excessive syneresis. However, in the present invention, if the polysaccharide is first dissolved in the alkaline aqueous phase, the sugar or polyol can be added in large amount without interfering with the subsequent gelation by means of a gaseous acid anhydride.

This feature is of particular importance in the formulation of desserts and confectionery items such as jellies, jams, gumdrops and the like. In such items, the sugar concentration is commonly 50–65% sugar or even higher. The term "sugar" is used generically and is meant to include carbohydrates or their derivatives commonly used as sweetening agents, e.g., monosaccharides, such as glucose, or corn syrup; disaccharides, such as cane or beet sugar, or mixtures of the two such as invert sugar, a mixture of glucose and fructose.

An example of such usage is demonstrated in Example 15.

EXAMPLE 15

A 1.25 g. portion of polysaccharide was dissolved in a solution of 1.25 g. of $Na_3PO_4$ in 85.5 ml. of water. To the solution was added 0.03 g. of fruit flavor, 0.01 g. of a certified food dye, and 162 g. of cane sugar. The mixture was then warmed gently with stirring until the sugar dissolved. The approximate composition of the resulting solution was 0.5% $Na_3PO_4$, 0.5% polysaccharide and 65% sugar, with the remainder being water, flavoring agent and food dye. This mixture was then placed in an atmosphere of $Co_2$ until it was completely gelled. The resulting clear firm jelly was of pleasing appearance, easily spreadable on bread and had a good taste and mouth feel.

What I claim and desire to protect by Letters Patent is:

1. A process for preparing a firm continuous body of a gel of a beta-1,3-glucan polysaccharide which comprises preparing a solution of said beta-1,3-glucan in an aqueous medium having a pH of at least about 10.5 and subjecting said solution under quiescent conditions to an atmosphere of a gaseous acid anhydride under conditions of time and gas pressure sufficient to cause said anhydride to diffuse through said solution and effect gelling.

2. The process of claim 1 wherein the gaseous acid anhydride is $CO_2$.

3. The process of claim 1 wherein the polysaccharide is present in the solution in a concentration of about 0.1 to 10%.

* * * * *